US010595779B2

(12) United States Patent
Laugstøl

(10) Patent No.: US 10,595,779 B2
(45) Date of Patent: Mar. 24, 2020

(54) VENTILATION MEASUREMENT DEVICES, METHODS AND COMPUTER PROGRAM PRODUCT

(71) Applicant: SweetZpot AS, Fornebu (NO)

(72) Inventor: Arne Laugstøl, Fornebu (NO)

(73) Assignee: SWEETZPOT AS, Fornebu (NO)

( * ) Notice: Subject to any disclaimer, the term of this patent is extended or adjusted under 35 U.S.C. 154(b) by 262 days.

(21) Appl. No.: 15/560,073

(22) PCT Filed: Mar. 18, 2016

(86) PCT No.: PCT/NO2016/050054
§ 371 (c)(1),
(2) Date: Sep. 20, 2017

(87) PCT Pub. No.: WO2016/153358
PCT Pub. Date: Sep. 29, 2016

(65) Prior Publication Data
US 2018/0078208 A1    Mar. 22, 2018

(30) Foreign Application Priority Data

Mar. 20, 2015 (NO) .................................. 20150351
Mar. 24, 2015 (NO) .................................. 20150372

(51) Int. Cl.
*A61B 5/08* (2006.01)
*A61B 5/091* (2006.01)
(Continued)

(52) U.S. Cl.
CPC .......... *A61B 5/6831* (2013.01); *A61B 5/0004* (2013.01); *A61B 5/0803* (2013.01);
(Continued)

(58) Field of Classification Search
CPC ........ A61B 5/0205; A61B 5/08; A61B 5/0803; A61B 5/0816; A61B 5/091; A61B 5/1135;
(Continued)

(56) References Cited

U.S. PATENT DOCUMENTS 4,960,118 A    10/1990 Pennock
5,454,376 A    10/1995 Stephens et al.
(Continued)

FOREIGN PATENT DOCUMENTS

FR          2353268 A1    12/1977

OTHER PUBLICATIONS

International Search Report and Written Opinion issued in PCT/NO2016/050054 dated Sep. 19, 2016.

*Primary Examiner* — Thaddeus B Cox
(74) *Attorney, Agent, or Firm* — Arent Fox LLP

(57) ABSTRACT

A ventilation measurement device includes a fastening mechanism capable of permanently or detachably fastening the ventilation measurement device to a belt which can be worn around a person's chest. The device includes a substrate coupled to the fastening mechanism and capable of receiving tensional forces transmitted from the flexible belt through the fastening mechanism. A strain gauge is mounted on said substrate and is configured to output a signal with a functional relationship with said tensional forces to a controller unit. The controller unit is configured to receive and process the signal to produce processed data from the strain gauge signal, and to control a transmitter configured to transmit processed data to an external receiver.

9 Claims, 7 Drawing Sheets

(51) Int. Cl.
  *A61B 5/00*    (2006.01)
  *A61B 5/113*   (2006.01)
  *A61B 5/087*   (2006.01)
  *G01B 7/16*    (2006.01)

(52) U.S. Cl.
  CPC ............ *A61B 5/087* (2013.01); *A61B 5/0816* (2013.01); *A61B 5/091* (2013.01); *A61B 5/1135* (2013.01); *A61B 5/6823* (2013.01); *A61B 5/7278* (2013.01); *A61B 5/742* (2013.01); *G01B 7/16* (2013.01); *A61B 2562/0261* (2013.01)

(58) Field of Classification Search
  CPC .... A61B 5/6802; A61B 5/6823; A61B 5/6831
  See application file for complete search history.

(56) References Cited

U.S. PATENT DOCUMENTS

| | | | |
|---|---|---|---|
| 7,942,824 B1 | 5/2011 | Kayyali et al. | |
| 2007/0293781 A1 | 12/2007 | Sims et al. | |
| 2007/0299325 A1* | 12/2007 | Farrell | A61B 5/0002 600/301 |
| 2012/0029299 A1 | 2/2012 | Deremer et al. | |
| 2014/0128710 A1* | 5/2014 | Nakamura | A61B 5/02438 600/390 |
| 2014/0275931 A1* | 9/2014 | Kato | A61B 5/02438 600/390 |

* cited by examiner

VENTILATION MEASUREMENT DEVICES, METHODS AND COMPUTER PROGRAM PRODUCT

CROSS-REFERENCE TO RELATED APPLICATIONS

This application is a National Stage entry of International Application No. PCT/NO2016/050054, filed Mar. 18, 2016, which claims priority to Norwegian Patent Application Nos. 20150351, filed Mar. 20, 2015, and 20150372, filed Mar. 24, 2015. The disclosures of the priority applications are hereby incorporated herein in their entirety by reference.

FIELD OF THE INVENTION

The present invention relates to ventilation measurement devices and methods. In particular, the invention relates to wearable devices capable of measuring ventilation based on measurement of the change in tension of a belt to be worn around the chest of a person and to methods for processing the data generated from such devices.

BACKGROUND

Heart rate monitors that can be worn in a belt attached around a person's chest have become popular by professional athletes as well as runners and others engaged in physical exercises where the heart rate provides information about the effects of a training program and allows a user to exercise according to a plan in order to optimize efficiency and measure results of the training program. Recently, heart rate monitors that can measure heartrate at the wrist has also become available. It is well known that additional information can be obtained by measuring ventilation and/or respiration, but devices capable of performing such measurements are bulky and mostly used in laboratories, for example spirometers and cannulas, which a person has to breathe through while running on a treadmill or using a stationary exercise bike.

Alternatives do exist, for example in the form of piezoelectric sensors, magnetic sensors and nasal/oral thermocouples, as well as chest belts with resistivity dependent on tension. The different alternatives are all associated with various disadvantages, such as bulkiness, inaccuracy, discomfort etc., and they are not commonly used during regular exercises.

Consequently, the information that can be derived from measurement of respiration or ventilation has been unavailable to a person during training, and impossible to utilize as a means of optimizing training efficiency or measuring the effects of a training program over time.

With respect to terminology it should be noted that while respiration normally refers to the exchange of gases, primarily $O_2$ and $CO_2$, ventilation refers to the transportation of air into and out of the lungs through inhalation and exhalation. These terms are sometimes used interchangeably, but in the present description an attempt has been made to maintain a certain consistency in their respective use. However, there are clear physiological links between the two and certain parameters of one may be calculated or estimated based on parameters of the other. Also, the term respiratory rate will be used because of its establishment through convention, even if the correct term is ventilatory rate.

SUMMARY OF THE INVENTION

A ventilation measurement device is provided, comprising a fastening mechanism capable of permanently or detachably fastening the ventilation measurement device to an elastic belt which can be worn around a part of a subject's torso that expands as a function of inhalation. A substrate is coupled to the fastening mechanism and capable of receiving tensional forces transmitted from the flexible belt through the fastening mechanism. A strain gauge is mounted on the substrate and configured to output a signal with a functional relationship with the tensional forces. A controller unit is configured to receive and process the signal and produce processed data therefrom, and a transmitter is configured to be controlled by the controller to transmit processed data to an external receiver.

In a first embodiment, the fastening mechanism includes two parts attached to respective ends of the substrate and to respective points of the belt. The substrate is according to this embodiment made from a polymer and is subjected to tensional forces transmitted from the belt as a function of the belt being stretched when the subject is inhaling air.

The ventilation measurement device according to this embodiment may further include a protective plate at at least one end of the substrate, which is configured to restrict movement to one direction and prevent rotational movement, primarily by cooperating with or being restricted by internal surfaces, lugs or ears of the casing of the device.

The attachment of the fastening mechanism to the substrate at at least one end of the substrate (i.e. at the at least one end of the substrate with the protective plate) may include a screw which passes through the protective plate, through a flexible ring which connects the screw to the casing, and into the fastening mechanism.

In a second embodiment the ventilation measurement device may include a fastening mechanism with a first part attached to one end of the substrate and a second part attached to a casing of the ventilation measurement device. The substrate may in this case be made from a metal, and be attached to the casing at an end not attached to the first part of the fastening mechanism. The substrate may be configured such that the strain gauge is subjected to tensional or compressional forces when tensional forces are transmitted from the flexible belt to the substrate. For example, the tensional forces transmitted from the flexible belt may be translated to bending forces in the substrate, and the strain gauge may be subjected to tensional of compressional forces depending on which side of the substrate it is attached to.

The attachment of the first part of the fastening mechanism to the one end of the substrate may include a screw which passes through a flexible ring which connects the screw to the casing, and into the fastening mechanism.

In a third embodiment a ventilation measurement device may include a fastening mechanism with two parts attached to the belt and electrically connected to the strain gauge, and the substrate (with the strain gauge), which in this case may be made from a polymer, is provided between two layers of the flexible belt. The strain gauge is configured to transmit signals electrically through the fastening mechanism to the controller unit.

The controller may be a microprocessor, and the microprocessor may be configured to sample signals received from the strain gauge and control the transmitter to transmit data with a functional relationship with tensional forces in the flexible belt.

According to another aspect of the invention, a computing device can be provided, comprising a microprocessor, a transmitter receiver connected to the microprocessor, a storage unit capable of holding instructions and data, and a display unit. The storage unit includes instructions enabling the microprocessor to receive data samples representative of tensional forces in a flexible belt worn by a person, determine maximum and minimum values from the received data samples, determine inhale time and breathing period from the temporal relationship of the data samples, calculate an estimated change in lung volume during inhalation based on the maximum and minimum values, calculate at least one of an estimated flow during inhalation, and estimated ventilation rate and an estimated oxygen uptake for the person wearing the flexible belt, and display information representative of the calculations on the display unit.

According to yet another aspect of the invention, a computer program product is provided. The computer program product may be stored on a computer readable medium and include instructions enabling a computer to process data samples representative of tensional forces in a flexible belt worn by a person. The computer may then determine maximum and minimum values from the received data samples, determine inhale time and breathing period from the temporal relationship of the data samples, calculate an estimated change in lung volume during inhalation based on the maximum and minimum values, calculate at least one of an estimated flow during inhalation, and estimated ventilation rate and an estimated oxygen uptake for the person wearing the flexible belt, and display information representative of the calculations on the display unit.

DETAILED DESCRIPTION

Figure 1:
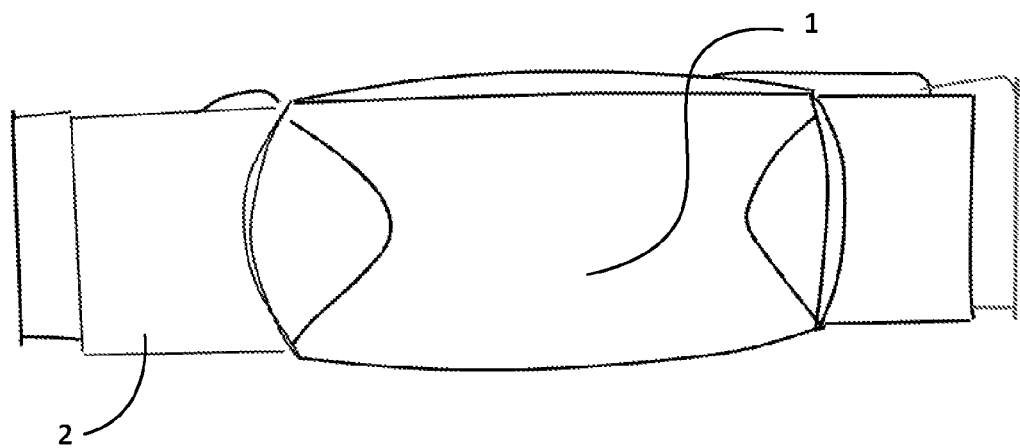
FIG. 1 is a device including a sensor unit and a flexible belt.

In the following description of various embodiments, reference will be made to the drawings, in which like reference numerals denote the same or corresponding elements. It should be noted that, unless otherwise stated, different features or elements may be combined with each other whether or not they have been described together as part of the same embodiment below. The combination of features or elements in the exemplary embodiments are done in order to facilitate understanding of the invention rather than limit its scope to a limited set of embodiments, and to the extent that alternative elements with substantially the same functionality are shown in respective embodiments, they are intended to be interchangeable, but for the sake of brevity, no attempt has been made to disclose a complete description of all possible permutations of features.

Furthermore, those with skill in the art will understand that the invention may be practiced without many of the details included in this detailed description. Conversely, some well-known elements or functions may not be shown or described in detail, in order to avoid unnecessarily obscuring the relevant description of the various implementations. The terminology used in the description presented below is intended to be interpreted in its broadest reasonable manner, even though it is being used in conjunction with a detailed description of certain specific implementations of the invention.

Reference is first made to FIG. 1, which shows a sensor unit 1 attached to an elastic belt 2 in a manner which is well known from heart rate monitors. According to a first aspect of the present invention, such a sensor unit may include a ventilation sensor in addition to or instead of a heart rate sensor.

Heart rate monitors are used to measure the heart rate during an exercise. Based on the measured heart rate, information about the effects of the exercise can be made known to the user, for example as an indication of the intensity level of the activities, the resting heart rate level, the maximum heart rate, etc.

Those with skill in the art will also be familiar with a technique called HRV (Heart Rate Variability). The heart beat interval of a human is not constant. There are small time variations between consecutive heart beats. When a person inhales and exhales, the heart rate will be affected very slightly. By analyzing HRV the respiration rate can be estimated. Of course, there is also other information that can be derived from HRV.

Figure 2:
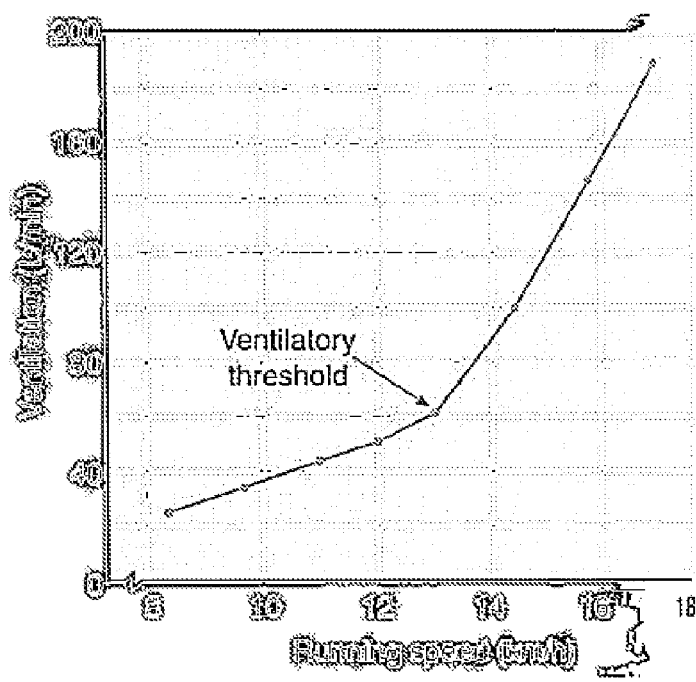
FIG. 2 is a diagram illustrating ventilatory threshold.

In general, the heart beat measurement itself contains certain amount of information, but is desirable to obtain additional information about the state of the body during exercise. In sport science, respiration is another very important factor. For example, the ventilatory threshold is a parameter it would be desirable to be able to monitor. The ventilatory threshold is the point at which ventilation starts to increase at a faster rate than the oxygen uptake. The concept is illustrated in the diagram in FIG. 2.

When the intensity level increases during an exercise, for example running speed increases, there is a point at which breathing becomes much more labored and respiration cannot deliver enough air to the body. This is a result of the body being unable to absorb as much oxygen as it needs, resulting in a deficiency of oxygen and rapid accumulation of lactate in the blood, which again causes increased ventilation. But increased ventilation will not solve the body's oxygen deficiency, and hence ventilation increases faster than oxygen uptake, which will reach its maximum at a point often referred to as $VO_2$ max.

Sometimes two different ventilatory thresholds are referred to, VT1—which is the point at which respiration rate begins to increase, and VT2—which is the point described above where ventilation starts to increase faster than oxygen uptake.

According to established sport science theory, most exercises should be performed below the ventilatory threshold (VT2), a modest amount should be performed at the ventilatory threshold, and a small but consistent amount should be performed above the ventilatory threshold.

In addition to estimation of ventilatory threshold, other parameters of interest can include respiration rate (RR). The RR can also be estimated by analysing HRV is no longer required, as with the invention, it can be more accurately measured.

In summary, to an end user, respiration activity measurement can become a very valuable addition for the heart rate measurement. With the respiration activities detection, additional useful and interesting features may be developed.

Figure 3:
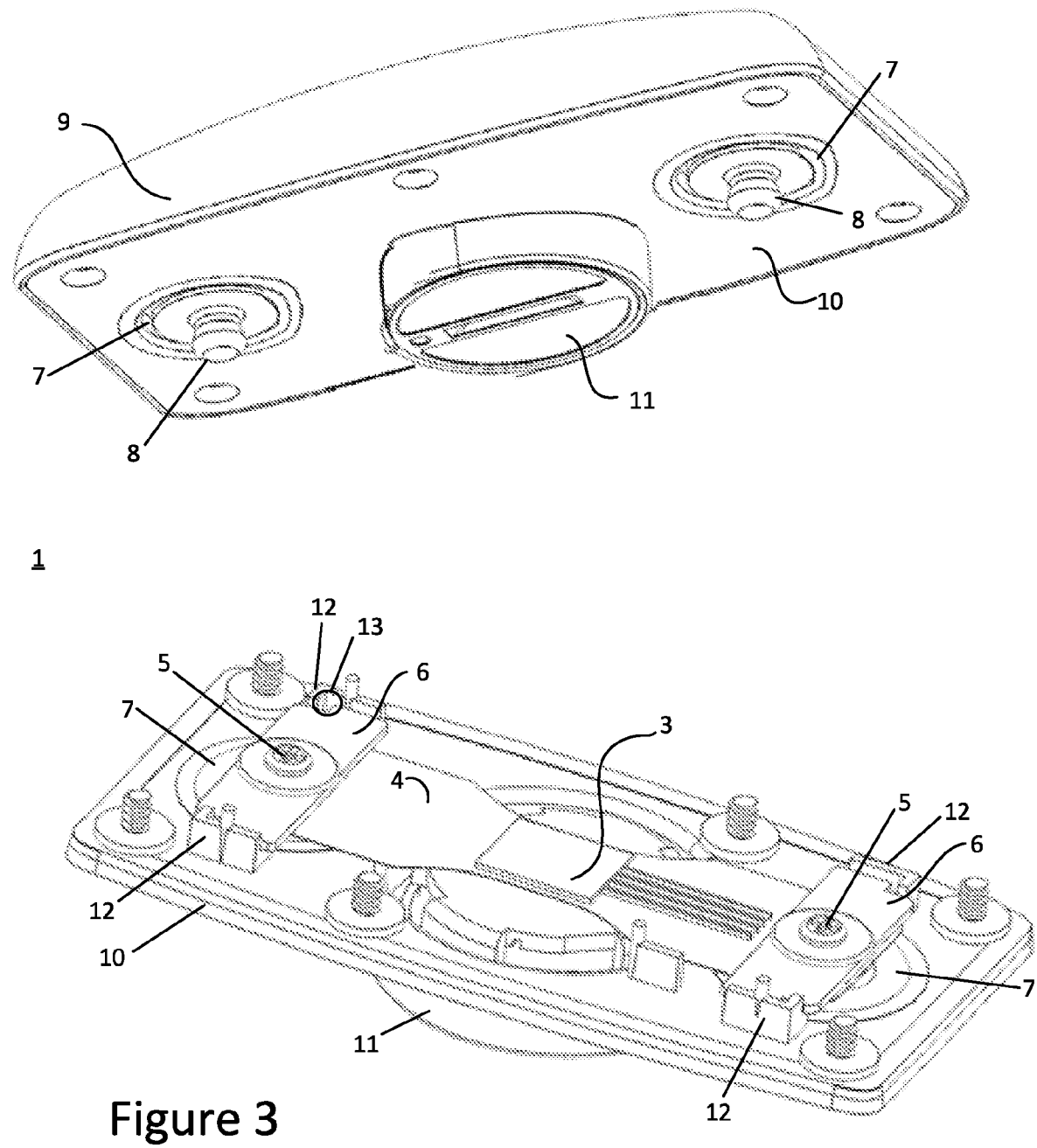
FIG. 3 shows two views of a first embodiment of a device according to the invention.

Turning now to FIG. 3, which shows two different views of a first embodiment of a sensor unit 1 consistent with the principles of the invention. According to an aspect of the invention, ventilation can be measured by the sensor unit 1 by providing a strain gauge 3 attached to a substrate 4. The strain gauge 3 measures the strain transferred from the belt 2 to the substrate 4 as a function of the wearer's breathing. When the wearer inhales, his/her chest will expand, and the tension in the belt 2 (FIG. 1) will increase. This increased tension is released when the wearer exhales.

In the embodiment illustrated in FIG. 3 the substrate 4 is a polymer substrate 4 upon which the strain gauge 3 is attached. The polymer substrate 4 is attached at each end to parts of the sensor unit 1 which engage with the belt 2. In the exemplary embodiment of FIG. 3, at either end of the substrate 4, a screw 5 passes through a protective plate 6, through the substrate 4 and through a flexible ring 7 before it enters and is fastened to a snap on button 8. The protective plate 6 is free to move in a longitudinal direction of the sensor unit 1, i.e. in the direction of tensional forces transmitted from the belt 2, and the flexible ring allows movement relative to a casing of the sensor unit 1. It will be understood by those with skill in the art that it is sufficient that only one of the ends of the substrate 4 is free to move relatively to the casing, and as such, that the connection from the other end of the substrate 4 to the belt may also be rigidly attached to the casing.

The flexible ring 7 may be made from rubber or some other organic or synthetic material that allows the required minimum movement relative to the casing.

The casing, which may be made from a plastic material, for example ABS, may consist of two halves, a front part 9 and a back part 10, wherein the back part has room for a battery 11 and other electronic circuitry, and the front part provides protection from the environment, and may also hold additional electronic circuitry. The two parts may be detachably or permanently attached to each other, for example by screws, as suggested in the drawing, by glue, tabs, or by any other means that is known in the art. A removable cover may be part of the room for a battery 11.

The electronic circuitry is not illustrated in FIG. 3, but may for example include a Wheatstone bridge or a similar electronic device for measuring small resistance changes connected to the strain gauge 3, an analog-to-digital converter including an amplifier circuit connected to the Wheatstone bridge, a memory with a look-up-table correlating sensor output with applied force, a Bluetooth transmitter, and potentially other components or modules that are known in the art, such as a controller module or microprocessor for controlling the operation of the sensor unit, memory circuits for storing data and/or instructions, a near field communication (NFC) module, a global positioning system (GPS) module etc. The operation of these components is well known in the art and they are not essential to the principles of the invention, so they will not be discussed in unnecessary detail. Their inclusion or omission may depend on design preferences and the capabilities of other equipment with which the sensor unit is configured to interact.

The back part 10 of the casing may also include protrusions such as tabs, ears or lugs that project from the inner surface of the back part in order to hold, support or guide the various internal parts of the sensor unit 2. The embodiment shown in FIG. 3 shows four such L-shaped protrusions 12 which together with the protective plates 6 prevent sideways motion of the substrate 4 and ensures that only transversal tension is transferred to the substrate 4 and thus to the strain gauge 3. The L-shaped protrusions 12 also serve as stoppers that establish a limit to transversal movement of the protective plates 6 and the substrate 4, preventing the substrate 4 from being stretched beyond an acceptable maximum. This maximum is determined by a tiny gap 13 between each L-shaped protrusion 12 and the corresponding protective plate 6. The size of the gap must be determined based on the elasticity of the substrate 4, the flexible rings 7 and the belt 2, as well as the sensitivity of the strain gauge 3, such that the sensor 1 can operate within the desired range of transmitted forces from the belt, but without causing damage or unnecessary wear to the substrate 4 and strain gauge 3.

It will be realized that when force is applied to the snap on button 8, this will be like applying a transversal force at one end of a beam, causing rotation. Since the beam in this case primarily consists of the screw 5 and the snap on button 8, this means that when the snap on button 8 is pulled outwards by the belt 2, the top of the screw 5 and the protective plate may tilt inwards. In order to prevent this, the front part 9 of the casing may be provided with protrusions that limit or prevent rotational movement by providing a surface along which the top of the screw 5 (or a corresponding washer) or the protective plate 6 can slide, but preventing rotational movement. Corresponding protrusions or surfaces may be part of the back part 10 of the casing. These protrusions are not illustrated in the drawing.

Figure 4A:
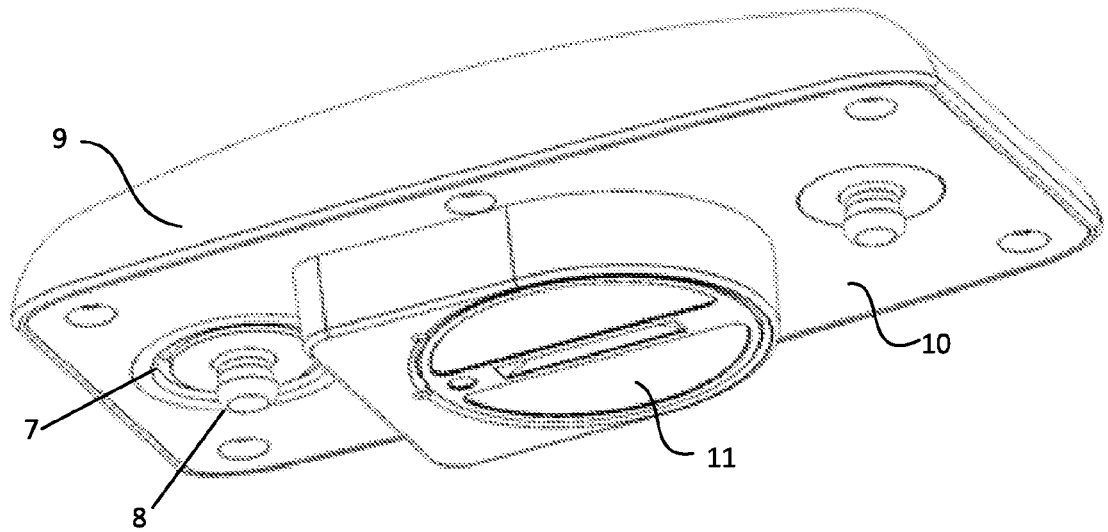
FIG. 4a shows two views of a second embodiment of a device according to the invention.
Figure 4A:
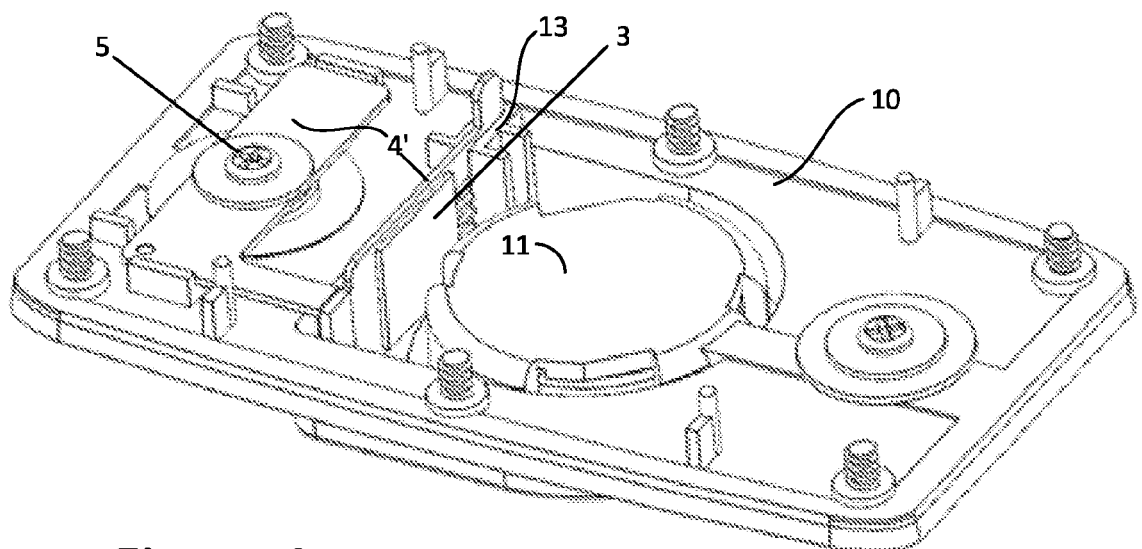

Reference is now made to FIG. 4a, which shows two corresponding views of a second embodiment of a sensor unit 1 consistent with the principles of the invention. This embodiment has many of the same features as the embodiment discussed with reference to FIG. 3, including a strain gauge 3, a substrate 4', a screw 5 which passes through the substrate 4' and a flexible ring 7 and is screwed into a snap on button 8. This embodiment also includes a front part 9 and a back part 10 of a casing and a battery holder 11, as well as necessary room for additional electronic circuitry (not shown). Unlike the first embodiment, the substrate 4' in this embodiment is made from a metal alloy, for example steel. The substrate 4' is attached to the hack part 10 of the casing, for example by being held inside a narrow gap between two protrusions 13, although other alternatives are possible, for example by gluing or using screws.

The substrate 4' is configured such that when a force is applied to the substrate 4' from the belt 2 (FIG. 1) through the snap button 8 and the screw 5, the part of the substrate 4' to which the strain gauge 3 is attached will bend. Several configurations of the substrate 4' may provide this functionality. In the drawing the strain gauge is attached to a surface of a first portion of the substrate 4' that is normal to the direction of the force transmitted from the belt 2, while the screw 5 passes through a second portion of the substrate 4' with a surface that is parallel to the direction of the applied force and attached to the first portion at the opposite end from the end that is attached to the back part 10 of the casing.

In this embodiment only one snap on button 8 is configured to transmit force to the substrate 4'. The snap on button and screw that only serve to provide attachment to the belt 2 are without reference numbers in order to avoid confusion an unnecessary clutter in the drawing.

The principles for measuring force by measuring deformation of a substrate (by stretching or bending) are well known in the art and will not be discussed in detail. Within the normal operating range of a device consistent with the principles of the invention, the deformation measured by the strain gauge will be proportional to the applied force from the belt. However, setting up a complete formula for how forces are transmitted through the entire configuration from belt to strain gauge is complicated, and an alternative is to create a look-up table which correlates sensor output with applied force based on the application of varying known forces.

Figure 4B:
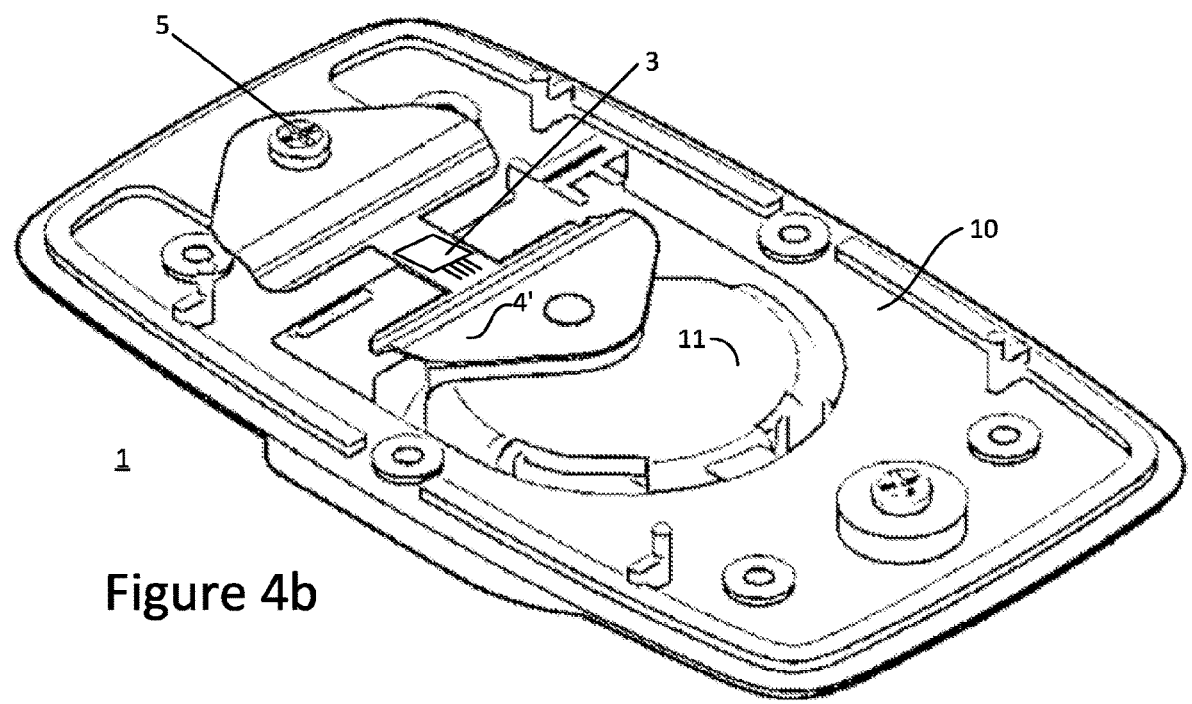
FIG. 4b shows an alternative configuration of the second embodiment.

FIG. 4b is a view of an alternative configuration of the second embodiment. In this configuration one end of the substrate 4' is attached to the hack part of the casing 10, for instance to the top of the room for the battery 11. The other end is attached with the screw 5 just like in the first configuration. The substrate 4' is substantially straight and flat between the to attachment points, but may be curved relative to its own plane such that when it is subject to stretching forces the covered sections will straighten. A strain gauge 3 may be attached to a section of the substrate that is particularly subject to deformation by stretching forces transmitted from the belt.

Figure 4C:
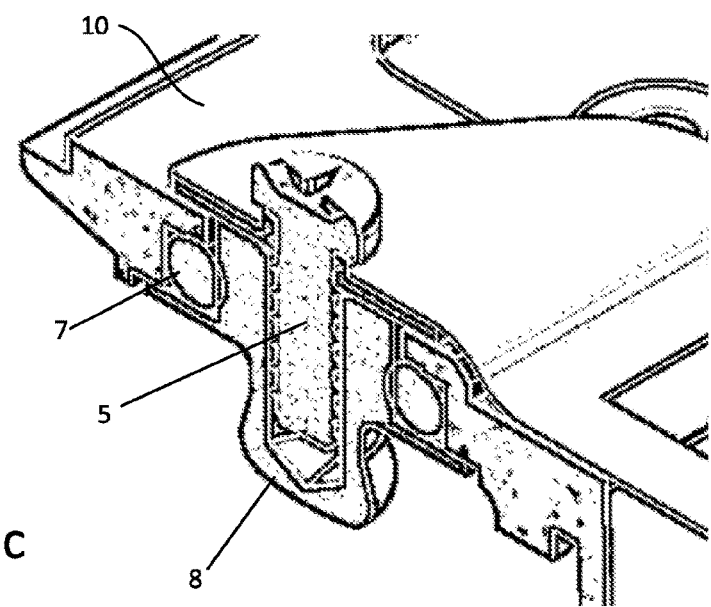
FIG. 4c is a detailed view of an embodiment of the fastening mechanism.

FIG. 4c is a detail view of the end of the substrate 4' which is attached to the screw 5 and snap on button 8. The screw enters the snap on button 8 which is mounted in a flexible ring 7. The flexible ring 7 holds the snap on button 8 while at the same time allowing it to move relatively to the back part of the casing 10. The flexible ring 7, which may be an o-ring, also serves as a watertight seal which prevents water from entering the device 1. This design can be adapted to all the embodiments described herein where the substrate is attached to the fastening mechanism and not to the casing.

It will b e realized by those with skill in the art that the screw 5 may be replaced with some other fastening device, for instance a metal post which passes through the substrate and into the snap button where it is riveted. Other alternatives include gluing and plastic welding.

Figure 5:
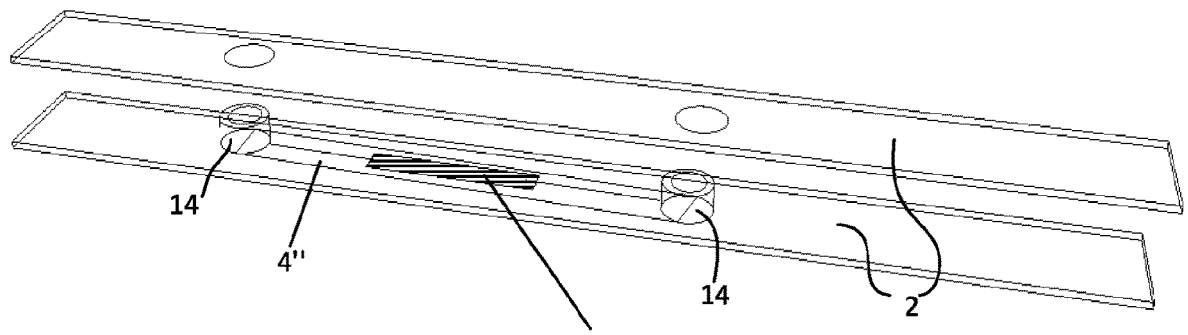
FIG. 5 shows parts of a flexible belt with a strain gauge mounted on a substrate embedded in the flexible belt.

FIG. 5 is an illustration of yet another embodiment of the invention, in which the strain gauge 3 is mounted on a polymer substrate 4" mounted between two layers of the belt 2. The substrate 4" is attached to two snap on buttons 14 which are configured to mate with corresponding snap on buttons on a device holding electronic circuitry, battery and other components. The electronic device is not shown, but may be shaped in the same manner as the sensor units 1 illustrated in FIG. 3 and FIG. 4, but without the components that have been moved to the belt 2. One or both of the snap on buttons on the device (corresponding to snap on buttons 8 must be free to move sufficiently so they do not prevent the relative movement of the snap on buttons 14 with respect to each other, such that force can be transmitted to the substrate 4". This may be achieved by use of one or two flexible rings corresponding to flexible rings 7 in FIG. 3 and FIG. 4.

In the drawing shown in FIG. 5, the substrate is provided between two snap on buttons. This may require that the sensor unit provides sufficient flexibility to allow the stretching forces in the belt to deform the substrate 4". An alternative is to provide the substrate 4" and the strain gauge 3 in a different part of the belt 2. This is possible provided that the opposite ends of the substrate is attached to the layers of the belt in a manner that transmits tensile forces in a consistent manner. The strain gauge 3 may still be electrically connected to the snap on buttons 8 for transmission of signals to the electronic circuitry in the sensor unit 1. Any other sensors provided in the belt 2, such as heart rate measurement electrodes, may transfer signals in the same manner through the snap on buttons 8.

It will be understood by those with skill in the art that while the strain gauge 3 measures deformation of the substrate 4, 4', 4", this deformation depends on the elasticity, dimensions and shape of the material from which the substrade is made and the amount of force transmitted to the substrate 4, 4', 4" from the belt 2, which again depends on the elasticity of the belt. Consequently, the belt and the substrate, as well as the parts that transmit force from the one to the other, must be designed to work well with each other. On the one hand it is desirable make the belt as flexible as possible in order to increase comfort for the person wearing the belt. On the other hand the belt must transmit sufficient force to the substrate to cause the desired deformation. In principle, the belt can be almost entirely without flexibility, provided that the substrate and other mechanisms in the sensor unit 1 is able to stretch sufficiently. For most instances, however, the belt is at least somewhat flexible, but a belt without elasticity combined with a sensor unit providing the necessary elasticity instead is within the scope of the invention. For most cases with a human subject, the combination belt and sensor unit should be capable of expanding approximately 2 to 3 cm during use.

Based on the measurement of force transmitted from the chest belt 2 it is possible to calculate ventilation. By assuming that the volume of the lungs can be approximated by a cylinder, the following relation between circumference and flow can be obtained:

$$A = \pi r^2$$

$$0 = 2nr$$

$$r = 0/2 \neq$$

$$r^2 = 0^2/4 \neq^2$$

$$V = A \cdot h = hnr^2$$

$$\text{Flow}(t) = \frac{\emptyset v}{\Delta t}$$

$$\text{Flow}(t) = \frac{h\pi(r_2^2 - r_1^2)}{\Delta t} = \frac{h\pi\left(\frac{O_2^2}{4\pi^2} - \frac{O_1^2}{4\pi^2}\right)}{\Delta t} = \frac{\frac{h}{4\pi}(O_2^2 - O_1^2)}{\Delta t}$$

Where A is the area defined by the circumference (assumed to be circular), O is the circumference, r is the radius, and V is the volume.

Assuming elastic and linear response to applied force in the stretched material, the force can be expressed as $$F = \frac{E \cdot A_O \cdot AO}{O_0}$$

where E is Young's modulus, $A_o$ is the area of cross section defined by the belt, $O_o$ is initial length of the belt and ØO is length increment. Assuming E, $A_o$ and $O_o$ is constant gives $$F = k_1 \cdot AO$$

where ki is a constant dependent on E, $A_o$ and $O_o$. This constant may be adjusted further based on calibration.

Figure 6:
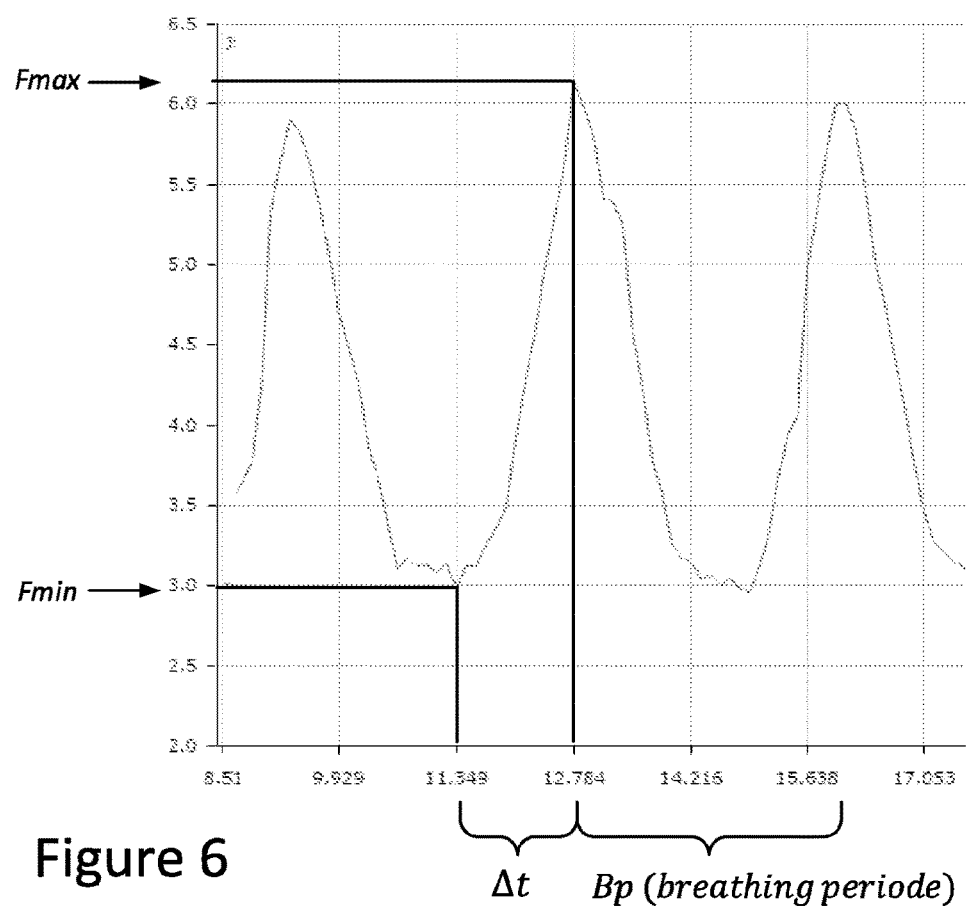
FIG. 6 is a diagram illustrating breathing as a function of time.

FIG. 6 shows a diagram illustrating an example of measured force as a function of time. These measurements provide the following values Fmax=6.2N
Fmin=3.0N
At=12.8 s–11.3 s=1.5 s
Bp=16.1 s–12.8 s=3.3 s
Br=llBp=1/3.3 s=0.3 Hz=18.1 breaths per minute where Fmax is maximum force measured, Fmin is minimum force measured, At is time to inhale, Bp is breath period (time to inhale plus time to exhale), and Br is breath rate.

Based on these numbers it is possible to establish an estimate for circumference, O, as follows.

$$O_{start} = 0.83 \text{ m}, k_i = 300, 1/k_i = 0.003$$

$$F_{max} = 6.2\text{N}, F_{min} = 3.0\text{N}, At = 1.5 \text{ s}$$

$$F = k_1 \cdot \Delta O$$

$$\Delta O = \frac{1}{k_1} \cdot F$$

$$O_{max} - O_{start} = \frac{1}{k_1} \cdot F_{max}$$

$$O_{max} = \frac{1}{k_1} \cdot F_{max} \sim O_{start} \Rightarrow 0.003 \cdot 6.2 + 0.83 \cong 0.85 \text{ m}$$

$$O_{min} = \frac{1}{k_1} \cdot F_{min} \sim O_{start} \, t \Rightarrow 0.003 \cdot 3.0 + 0.83 = 0.09 + 0.83 \cong = 0.84 \text{ m}$$

where $O_{start}$ is the circumference of the belt when it is adjusted to fit the wearer, but not actually worn (i.e. there are no stretching forces at work), $O_{max}$ is the maximum circumference i.e. when the maximum force, $F_{max}$ is measured by the sensor, $O_{min}$ is the minimum circumference i.e. when the minimum force, $F_{min}$ is measured by the sensor. $O_{start}$ will depend on the adjustment of the belt made by the user, and the device may allow for individual calibration by entering this value for example over a Bluetooth interface. However, in some embodiments of the invention, the belt may not allow adjustment and operate with a fixed circumference which is known in advance, or only a minimum of adjustment may be possible and the margin of error introduced by this adjustment may be considered acceptable.

Based on the values above, flow can be calculated as $$\text{Flow}(t) = \frac{\frac{h}{4\pi}(O_{max}^2 - O_{min}^2)}{\Delta t} \Rightarrow \frac{\frac{h}{4\pi}(0.85^2 - 0.84^2)}{\Delta t} \Rightarrow 0.27 \frac{\text{liter}}{\text{second}}$$

The flow calculated here as $0.27_{1/s}$ is the rate at which air flows into the lungs during inhalation. To determine air intake over time, i.e. ventilation, this value must be multiplied with the ratio At/Bp.

The electronic circuitry of the sensor unit 1 includes a controller which is capable of sampling the output of the strain gauge with a sampling rate at least twice the maximum breathing rate (or, since inhalation time is typically shorter than exhalation time, a frequency that is at least $1/At_{min}$), where $At_{min}$ is the shortest expected inhalation time. Respiratory rate during exercise will typically reach a level of approximately 30 breaths per minute, but may go significantly higher at high levels of exhaustion, and may reach levels as high as 60 breaths per minute or more, which translates to a sampling rate of at least 2 Hz.

However, the breathing signal delivered from the strain gauge may include higher frequency components and in some embodiments of the invention the signal form the strain gauge is filtered with a low pass filter at somewhere in the range of 7-10 Hz, which requires a sampling rate of 14-20 Hz. It may, however, be desirable to track the signal more closely in order to simplify the algorithms used to detect the maximum and minimum values. For this purpose a sampling rate of 100 Hz has been found suitable. On the other hand, higher sampling frequency increases power consumption in the sensor unit and it may therefore be desirable to reduce the number of samples. In some embodiments of the invention, low power electronics detect the minimum and maximum values of the signal and send an interrupt to the controller, which may be a microprocessor or CPU, such that the controller operates at high power only near the maximum and minimum values of the signal and revert to a low power mode in between.

Sampling rate is consequently a design parameter that must be chosen based on the range of respiratory rates the device should be able to measure.

It will be realized by those with skill in the art that adjustments to the equations presented above may be made based on calibration, for example in order to offset errors introduced by the assumption that the volume, V, is a cylinder with radius r=O/2.

Figure 7:
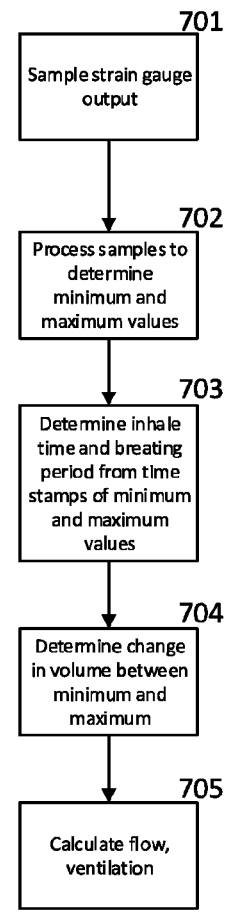
FIG. 7 is a flowchart illustrating a method of calculating breathing parameters from data derived from a device according to the invention.

FIG. 7 illustrates in a flow chart a method of calculating ventilation based on measurements performed with a device consistent with the principles of the invention. It should be understood that this flowchart by necessity have to show the steps in sequence, but that some of the steps may be performed in a different sequence or simultaneously. Equally well, some steps may be performed in the sensor unit while other steps are performed in a receiving unit. Some steps may even be performed partially in the receiver unit in order to reduce the amount of data that is transmitted to the receiving unit, for example in order to conserve power used for transmission, and the calculations may then be completed in the receiving unit. Additional steps such as filtering, may also be performed.

In a first step 701 the output form the strain gauge 3 sampled in order to produce a digital signal that can be processed further. Sampling rate has been discussed above, and the number of bits per sample may be 12, although other alternatives, such as 8, 10 or 16 bits/sample, are within the scope of the invention.

In a following step 702 the samples are processed in order to detect minimum and maximum values. This may be performed using derivation, using mathematical methods that are well known in the art.

Based on the detection of maximum and minimum values, significant points in time may be detected in step 703 and the inhalation time At and breathing period Bp may be determined. The values produced by these calculations may then be used in step 704 to determine an estimate of change in lung volume during inhalation, $\Delta V$. From this result, further refinements may be calculated in step 705, such as flow during inhalation, total ventilation (e.g. expressed as liters/minute), oxygen uptake $VO_2$, ventilation threshold, lactate threshold etc. The mathematics involved in these calculations when the results explained above are provided, are well known and will not be described in further detail.

Figure 8:
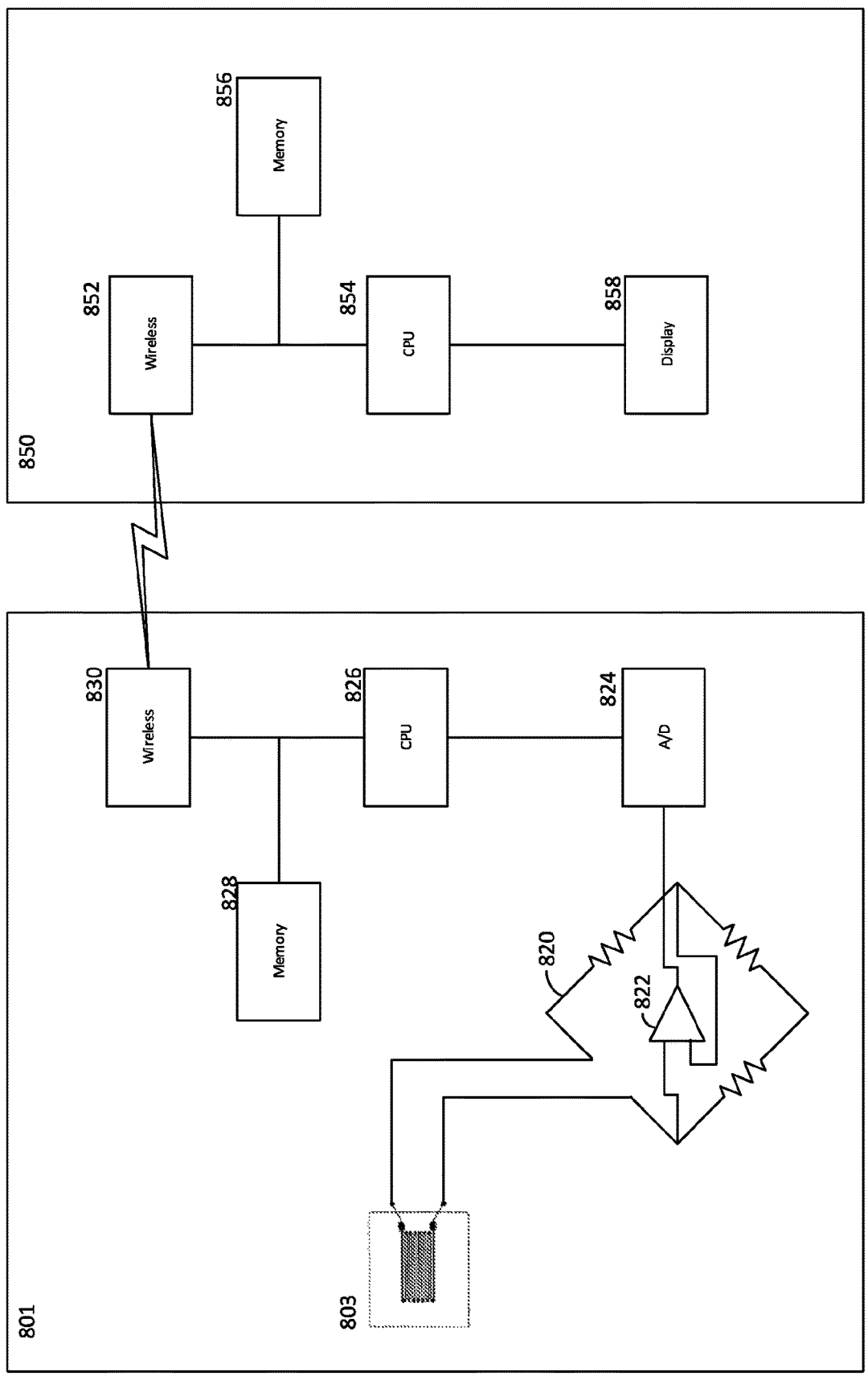
FIG. 8 is a block diagram illustrating the electronic circuitry of devices operating in accordance with one aspect of the disclosure.

Turning now to FIG. 8, which is a drawing depicting a block diagram of the most important modules of the electronic circuitry of devices operating according to the invention. The drawing includes two main units, a sensor unit 801 and a computing device 850. The sensor unit 801 includes a strain gauge 803 connected to a Wheatstone bridge 820. The Wheatstone bride 820 is connected to an amplifier 822 which delivers a signal to an analog-to-digital converter 824. The digital signal is sampled by a controller 826 which may be a microprocessor. The controller may operate in accordance with instructions stored in local memory 828, although other hardware/software combinations are possible, as discussed above. The controller and the memory 828 may communicate over a signal bus which is also connected to a wireless unit 830, which may for example be a Bluetooth device.

The wireless unit 830 is able to establish a communication link with a corresponding wireless unit 852 in computing unit 850. The computing unit 850 includes another microprocessor 854 and local memory 856, all communicating over a bus. The computing unit may also include a display device 858 as well as other user interface components (not shown) such as a loudspeaker, input buttons, a keyboard, a touch interface etc.

The further capabilities of the computing unit 852 regarding computation of parameters have been discussed above and will not be repeated here.

In some embodiments of the invention the calculations are performed in the sensor unit 1.1n these embodiments the electronic circuitry of the sensor unit 1 may include a microprocessor, a microcontroller, an ASIC or some other type of system-on-chip (SoC), for example a field-programmable gate array (FPGA) capable of performing the necessary calculations. It will be understood that the sensor unit may include such circuitry even if these calculations are performed external to the sensor unit 1. The sensor unit 1 must at least include sufficient circuitry to perform analog/digital conversion and the capability of transmitting samples in a manner that preserves sufficient information regarding both measured force and time to enable the receiving device to perform the calculations described above.

According to other embodiments of the invention the sensor unit 1 may be configured to transmit raw measurement data to an external device which is configured to perform the calculations.

In either case, the sensor unit 1 may be capable of transmitting data to a device worn by the person wearing the sensor unit 1 and the belt 2. This device may be substantially similar to devices known in the art for receiving HRM data, and indeed the device may include some or all of the capabilities of such a HRM device, just as the sensor unit 1 and the belt 2 may include HRM capabilities in combination with the features provided by the invention. In some embodiments, however, the sensor unit 1 may be configured to simply store date during exercise and allow the data to be downloaded for example to a computer after the exercise has been completed.

The method described above may, according to the invention, be embodied in a computer program product which is stored in a computer readable memory or installed in a device which is capable of receiving data from the sensor unit 1 for example using a Bluetooth link. Such a device may be a wearable device which is capable of performing the calculations in real time and display the results on a display or produce audible signals indicating operation within or outside a desirable range. Equally well, the device may be a general purpose computer such as a PC which is capable of downloading the data after an exercise is completed and perform calculations and present results to the user at that time.

Many additional variations are possible within the scope of the invention. For example, the strain gauge may b e a semiconductor strain gauge, but other alternatives include the foil gauge type, the piezoresistor type or any other type of strain gauge known in the art. Other details may also vary from the examples used in this description. For example, the snap on buttons may be replaced by other fastening devices known in the art. Equally well, the sensor unit may be an integrated part of the belt, and not detachable. Similarly, the belt may be part of a larger harness such as a sports bra, an elastic shirt or some other wearable device which transmits force as a function of expansion of the chest of a wearer while breathing. As such, the term belt should be understood as any garment which encircles the chest or stomach of the wearer, even if the actual belt shape is integrated into another garment.

While the various embodiments have been described for use by a human subject, the invention may also be adapted to other large mammals, such as a racing horse or a racing dog, and the belt may be worn around a part of the torso of the subject that expands and contracts as a function of the subject's breathing, which in most cases means the chest and part of the stomach.

In the embodiments described with reference to FIG. 3 and FIG. 4, the force is transmitted from the belt to the substrate by way of the mechanism including a snap on button 8, a screw 5 and, with respect to FIG. 3, a protective plate 6, and the mechanism is coupled to the casing with a flexible ring 7. Other alternatives are possible within the scope of the invention, including permanent attachment to the belt by glue, molded plastic, or sewing, and with a flexible attachment to the casing of the sensor device using plastic or metal parts that are free to slide relatively to each other, that include springs or other flexible material such as foam rubber.

A note was made above about the difference between respiration and ventilation. There is a tendency in the art to use these terms interchangeably, and the adoption of the usage that has been adhered to herein should not be interpreted in a manner that imposes unintended limitations on the invention.

What is claimed is:

1. A ventilation measurement device, comprising:
    a fastening mechanism capable of permanently or detachably fastening the ventilation measurement device to a belt which can be worn around a part of a subject's torso that expands as a function of inhalation;
    a substrate coupled to the fastening mechanism and capable of receiving tensional forces transmitted from the belt through the fastening mechanism;
    a strain gauge mounted on said substrate and configured to output a signal with a functional relationship with said tensional forces;
    a controller unit configured to receive and process said signal and produce processed data therefrom; and
    a transmitter configured to be controlled by said controller unit to transmit the processed data to an external receiver;
    wherein said fastening mechanism includes a first part attached directly to a first end of said substrate and a second part attached either:
        directly to a second end of said substrate in order to transmit tensional forces directly to the substrate, or
        directly to a casing in order to transmit the tensional forces to the second end of said substrate, said second end of said substrate being attached directly to the casing; and
    an attachment of the first part of said fastening mechanism passes through a flexible ring which connects the fastening mechanism to the casing while allowing the first part of the fastening mechanism to move relative to the casing in order to transmit the tensional forces to the substrate.

2. The ventilation measurement device according to claim 1, wherein:

said first part and said second part of said fastening mechanism are respectively attached to the first end and the second end of said substrate and to respective points of said belt; and said substrate is made from a polymer and is subjected to the tensional forces transmitted from said belt, as a function of the belt being stretched.

3. The ventilation measurement device according to claim 2, further comprising;
a protective plate at at least one of the first end and the second end of said substrate, which is configured to restrict movement to one direction and prevent rotational movement; and
wherein the attachment of said fastening mechanism to said substrate at a same end or same ends of the substrate as the protective plate, which includes a screw which passes through said protective plate, through the flexible ring which connects the screw to the casing, and into said fastening mechanism.

4. The ventilation measurement device according to claim 1, wherein:
said second part is attached to the casing; and
said substrate is made from a metal, is attached to said casing at an end not attached to said first part of said fastening mechanism, and is configured such that said strain gauge is subjected to tensional or compressional forces when the tensional forces are transmitted from said belt to said substrate.

5. The ventilation measurement device according to claim 4, wherein the attachment of said first part of said fastening mechanism to said first end of said substrate includes a screw which passes through the flexible ring which connects the screw to the casing, and into said fastening mechanism.

6. The ventilation measurement device according to claim 1, wherein said controller unit is a microprocessor.

7. The ventilation measurement device according to claim 6, wherein said microprocessor is configured to sample signals received from said strain gauge; and control said transmitter to transmit data with a functional relationship with tensional forces in said belt.

8. The ventilation measurement device according to claim further comprising:
a microprocessor;
a transmitter receiver connected, to said microprocessor;
a storage unit capable of holding instructions and data; and
a display unit;
wherein said storage unit includes instructions enabling said microprocessor to:
receive data samples representative of tensional forces in said belt;
determine maximum and minimum values from said data samples,
determine inhale time and breathing period from a temporal relationship of said data samples;
calculate, an estimated change in lung volume during inhalation based on said maximum and minimum values;
calculate at least one of an estimated flow during inhalation, an estimated ventilation rate, an estimated oxygen uptake, or a ventilatory threshold for a person wearing said belt; and
display information representative of said calculations on said display unit.

9. A computer program product stored on a computer readable medium and including instructions enabling a computer to process data samples representative of tensional forces in the belt worn around a part of a person's torso that expands as a function of inhalation, said data samples being obtained by the ventilation measurement device according to claim 1, wherein the processing comprises:
determining a maximum and minimum value from said data samples;
determining inhale time and breathing period from a temporal relationship of said data samples;
calculating an estimated change in lung volume during inhalation based on said maximum and minimum value;
calculating at least one of an estimated flow during inhalation, an estimated ventilation rate, an estimated oxygen uptake, or a ventilatory threshold for the person wearing said belt; and
displaying information representative of said calculations on a display unit.

* * * * *